United States Patent [19]

Frankel et al.

[11] 4,341,712
[45] Jul. 27, 1982

[54] FLUORODINITRO COMPOUNDS

[75] Inventors: Milton B. Frankel, Tarzana; Edward F. Witucki, Van Nuys, both of Calif.

[73] Assignee: Rockwell International Corporation, El Segundo, Calif.

[21] Appl. No.: 769,748

[22] Filed: Feb. 17, 1977

[51] Int. Cl.³ .......................................... C07C 117/00
[52] U.S. Cl. ..................................... 260/349; 149/88; 564/122; 568/307; 568/589
[58] Field of Search .......... 149/88; 260/349, 583 NH, 260/593 H, 614 F, 615 BF; 568/305, 589, 307; 564/122

[56] References Cited

U.S. PATENT DOCUMENTS

| | | | |
|---|---|---|---|
| 3,387,044 | 6/1968 | Grakauskas et al. | 149/88 X |
| 3,873,626 | 3/1975 | Adolph | 149/88 X |
| 3,907,907 | 9/1975 | Frankel et al. | 149/88 X |
| 3,922,311 | 11/1975 | Peters et al. | 149/88 X |
| 3,946,085 | 3/1976 | Adolph | 149/88 X |
| 4,001,291 | 1/1977 | Adolph | 149/88 X |

*Primary Examiner*—Leland A. Sebastian
*Attorney, Agent, or Firm*—H. Fredrick Hamann; Harry B. Field

[57] ABSTRACT

Fluorodinitro compounds are proposed as new compositions of matter which are useful as energetic ingredients for propellant and explosive formulations.

7 Claims, No Drawings

FLUORODINITRO COMPOUNDS

BACKGROUND OF THE INVENTION

1. Field of the Invention

The development of advanced solid propellants, gun propellants and explosives requires the use of energetic, stable ingredients, including the oxidizer, binder and plasticizer. These ingredients must have a favorable preferably positive heat of formation and be oxygen-rich in order for a high performance to be met. Unfortunately, such compounds are not readily available. Moreover, these ingredients must have thermal and shock stability in order to permit safe storage and handling.

These disadvantages of the prior art are overcome with the present invention and new compositions of matter are proposed which are readily available and which are highly advantageous when formulated into propellant or explosive compositions.

The advantages of the present invention are preferably attained by providing fluorodinitro compounds as new compositions of matter. These compounds are found to have low volatility and extremely high heats of formation, while having low melting points. Thus, these compounds are well suited for use as plasticizers in propellant or explosive formulations.

Accordingly, it is an object of the present invention to provide fluorodinitro compounds as new compositions of matter.

Another object of the present invention is to provide improved ingredients for formulating propellants and explosives.

A specific object of the present invention is to provide fluorodinitro compounds as ingredients for propellant and explosive formulations.

These and other objects and features of the present invention will be apparent from the following detailed description.

DETAILED DESCRIPTION OF THE INVENTION

In the form of the invention chosen for purposes of illustration, fluorodinitro compounds are proposed as new compositions of matter having utility as ingredients of propellant or explosive formulations.

EXAMPLE I 1,2-Dibromo-3-fluorodinitroethoxypropane

A solution of 100 g (0.515 m) of allyl fluorodinitroethyl ether in 200 ml of carbon tetrachloride was cooled in an ice bath and 99 g (0.62 m) of bromine was added. The mixture was stirred at ambient temperature overnight, refluxed for several hours and concentrated to give 172.9 g (94.8%) of amber liquid, $n_D^{24}=1.4998$, purity=95.7% by G.C. distillation at 123°/0.25 m gave a colorless liquid, $n_D^{26}=1.5010$, with a G.C. purity of 100%.

EXAMPLE II 1,2-Diazido-3-fluorodinitroethoxypropane (DAFP)

A mixture of 114.5 g (0.32 m) of 1,2-dibromo-3-fluorodinitroethoxypropane, 65 g (1.0 m) of sodium azide, and 400 ml of dimethyl formamide was heated with stirring at 70°–80° for three days. Methylene chloride, 300 ml, was added and the mixture was washed with water until free of dimethyl formamide. Concentration of the solution gave 19 g of amber liquid $n_D^{28}=1.4930$. The product was purified by column chromatography with carbon tetrachloride solvent on basic alumina to give a yellow liquid, $n_D^{25}=1.4832$.

| Elemental Analysis | | | |
|---|---|---|---|
| | C | H | N |
| Calculated for $C_5H_7FN_8O_5$: | 21.58 | 2.52 | 40.29 |
| Found: | 21.12 | 2.76 | 39.63 |

The properties of DAFP are summarized in Table I.

TABLE I

| | |
|---|---|
| NAME: | 1,3-Diazido-3-fluorodinitroethoxypropane |
| CODE: | DAFP |
| STRUCTURE: | $FC(NO_2)_2CH_2OCH_2CHCH_2N_3$ with $N_3$ on middle C |
| FORMULA: | $C_5H_7FN_8O_5$ |
| MOLECULAR WEIGHT: | 278 |
| REFRACTIVE INDEX: | 1.4832 @ 25° C. |
| DENSITY: | 1.44 g/cc |
| MELTING POINT: | Glasses at −30° C. |
| DSC: | |
| ENDOTHERM | 183° C. |
| EXOTHERM: | 185° C. |
| WEIGHT LOSS AT 73° C.: (24 hrs) | 7.2% (FEFO — 12%) |
| $\Delta H_F$: | +88 kcal/mole |

EXAMPLE III

Bis[5,5,5-fluorodinitro-2,2-bis-(difluoroamino)-pentyl] trifluoroacetal (SYTA)

A mixture of 2.32 g (0.02 mole) of trifluoroacetaldehyde hydrate, 11.9 g (0.04 mole) of 5,5,5-fluorodinitro-2,2-bis(difluoroamino)-pentanol, and 50 ml of trifluorosulfamic acid and 2.0 ml of methylene chloride was stirred overnight at ambient temperature, refluxed for 72 hours, and poured on ice. The aqueous mixture was extracted with methylene chloride, washed with water, base, and water, and passed through a basic alumina column. The solution was concentrated to give 1.0 g of light yellow oil, $n_D^{25}=1.4108$.

| Elemental Analysis: | | |
|---|---|---|
| | C | H |
| Calculated for $C_{12}H_{13}F_{13}N_8O_{10}$: | 21.30 | 1.92 |
| Found: | 21.69 | 1.76 |

EXAMPLE IV

3-Fluorodinitroethoxy-1-chloro-2-propanol

A mixture of 347 g (1.4 moles) of glycidyl fluorodinitroethoxide which can be prepared by method of U.S. Pat. No. 3,907,907, 2 ml of water, and 570 ml (7.0 moles) of 37% hydrochloric acid was stirred overnight at ambient temperature. The mixture was extracted with 500 ml of methylene chloride. The methylene chloride solution was washed with water, dried, and concentrated to give 299 g (86.6%) of light yellow liquid, $n_D^{25}=1.4562$. G.C. analysis showed a purity of 88.3%.

EXAMPLE V

3-Fluorodinitroethoxy-1-chloroacetone

To a solution of 299 g (1.21 moles) of 3-(fluorodinitroethoxy)-1-chloro-2-propanol in 500 ml of acetone was added a solution of 121 g (1.21 moles) of chromic oxide, 200 ml of water, and 65 ml (1.21 moles) of 96% sulfuric acid. The reaction mixture was stirred for several hours at ambient temperature. The upper layer was separated, washed with water, bicarbonate, and water, dried, and concentrated to give 73 g of light yellow liquid, $n_D^{24}=1.4598$. G.C. analysis showed purity of 86.5%.

EXAMPLE VI

1-Chloro-2,2-bis(difluoramino)-3-fluorodinitroethoxy Propane (CDFP)

To a solution of 100 ml (0.35 mole) of difluorosulfamic acid and 200 ml of methylene chloride was added a solution of 24.4 g (0.1 mole) of 3-fluorodinitroethoxy-1-chloroacetone in 100 ml of methylene chloride in 45 minutes. The reaction temperature rose from 20.5° to 29° C. The mixture was stirred two hours at ambient temperature. The methylene chloride layer was separated, washed with water, bicarbonate, and water, dried, and concentrated to give 24.2 g (72.8%) of colorless liquid, boiling point 70 C/0.1 mm, $n_D^{24}=1.4258$, $d^{25}$ 1.62. G.C. analysis showed only one peak.

| Elemental Analysis: | | | | |
|---|---|---|---|---|
| | C | H | Cl | N |
| Calculated for $C_5H_6F_5ClN_4O_5$: | 18.05 | 1.81 | 10.68 | 16.84 |
| Found: | 17.33 | 1.89 | 10.38 | 16.22 |

EXAMPLE VII

1-Azido-2,2-bis(difluoramino)-3-fluorodinitroethoxypropane (ADFP)

A mixture of 1.7 g of 1-chloro-2,2-bis(difluoramino)-3-fluorodinitroethoxypropane, 0.7 g of sodium azide, 10 ml of acetone, and 5 ml of water was refluxed for 72 hours. The mixture was extracted with methylene chloride, washed with water, and concentrated to give 1.3 g of light yellow liquid. I.R. showed an absorption for azide at 4.7µ.

These materials have been found to have high thermal stability and exceptionally high heats of formation, as indicated in Table I. Consequently, these materials are excellent candidates as ingredients for propellant or explosive formulations.

Obviously, numerous variations and modifications may be made without departing from the present invention. Accordingly, it should be clearly understood that the forms of the present invention described above are illustrative only and are not intended to limit the scope of the invention.

We claim:

1. A new composition of matter selected from the group consisting of:
    1,2-dibromo-3-fluorodinitroethoxypropane,
    1,2-diazido-3-fluorodinitroethoxypropane,
    fluorodinitroethoxyl-1-chloro-2-propanol,
    3-fluorodinitroethoxy-1-chloracetone,
    1-chloro-2,2-bis(difluoramino)-3-fluorodinitroethoxypropane, and
    1-azido-2,2-bis(difluoramino)-3-fluorodinitroethoxypropane.

2. The composition of claim 1 wherein:
    said compound is 1,2-dibromo-3-fluorodinitroethoxypropane.

3. The composition of claim 1 wherein:
    said compound is 1,2-diazido-3-fluorodinitroethoxypropane.

4. The composition of claim 1 wherein:
    said compound is fluorodinitroethoxyl-1-chloro-2-propanol.

5. The composition of claim 1 wherein:
    said compound is 3-fluorodinitroethoxy-1-chloroacetone.

6. The composition of claim 1 wherein:
    said compound is 1-chloro-2,2-bis(difluoramino)-3-fluorodinitroethoxypropane.

7. The composition of claim 1 wherein:
    said compound is 1-azido-2,2-bis(difluoramino)-3-fluorodinitroethoxypropane.

* * * * *